(12) United States Patent
Erhard et al.

(10) Patent No.: US 10,827,986 B2
(45) Date of Patent: Nov. 10, 2020

(54) COMPUTING AND DISPLAYING A SYNTHETIC MAMMOGRAM DURING SCANNING ACQUISITION

(71) Applicant: KONINKLIJKE PHILIPS N.V., Eindhoven (NL)

(72) Inventors: Klaus Erhard, Hamburg (DE); Frank Bergner, Hamburg (DE); Hanns-Ingo Maack, Norderstedt (DE)

(73) Assignee: KONINKLIJKE PHILIPS N.V., Eindhoven (NL)

(*) Notice: Subject to any disclaimer, the term of this patent is extended or adjusted under 35 U.S.C. 154(b) by 149 days.

(21) Appl. No.: 16/060,428

(22) PCT Filed: Dec. 15, 2016

(86) PCT No.: PCT/EP2016/081098
§ 371 (c)(1),
(2) Date: Jun. 8, 2018

(87) PCT Pub. No.: WO2017/108549
PCT Pub. Date: Jun. 29, 2017

(65) Prior Publication Data
US 2018/0360395 A1 Dec. 20, 2018

(30) Foreign Application Priority Data
Dec. 21, 2015 (EP) .................................... 15201478

(51) Int. Cl.
*A61B 6/00* (2006.01)
*A61B 6/02* (2006.01)
(Continued)

(52) U.S. Cl.
CPC .............. *A61B 6/025* (2013.01); *A61B 6/502* (2013.01); *G06T 11/006* (2013.01);
(Continued)

(58) Field of Classification Search
CPC .................................. A61B 6/00; G06T 11/00
(Continued)

(56) References Cited

U.S. PATENT DOCUMENTS 7,245,694 B2 * 7/2007 Jing ....................... A61B 6/025
378/37
2008/0181355 A1 7/2008 Hemmendorff
(Continued)

FOREIGN PATENT DOCUMENTS

CA 2360656 4/2002
EP 2213234 8/2010
(Continued)

OTHER PUBLICATIONS

Åslund et al in "AEC for scanning digital mammography based on variation of scan velocity", Medical Physics, 32(11), 2005, pp. 3367-3374.

*Primary Examiner* — Abolfazl Tabatabai
(74) *Attorney, Agent, or Firm* — Larry Liberchuk

(57) ABSTRACT

An image processing apparatus (IP) comprising an input port (IN) for receiving projection data through respective 3D locations in an imaging region, said projection date collected in a scan operation by an imaging apparatus (IM). An image segment generator (IGS) of said apparatus (IP) is configured to generate, based on said projection data, a first image segment for said 3D locations. A visualizer (VIZ) configured to effect displaying said first image segment on a display device before or whilst the image apparatus collects projection data for a different 3D location.

14 Claims, 5 Drawing Sheets

(51) Int. Cl.
   *G06T 11/00*          (2006.01)
   *A61B 5/00*           (2006.01)
(52) U.S. Cl.
   CPC ....... *G06T 11/008* (2013.01); *G06T 2211/424* (2013.01); *G06T 2211/428* (2013.01)
(58) Field of Classification Search
   USPC ........................................................ 382/131
   See application file for complete search history.

(56) References Cited

U.S. PATENT DOCUMENTS

2010/0020929 A1* 1/2010 Akahori ............... A61B 6/4233
                                                          378/62
2010/0189330 A1   7/2010 Akahori
2013/0148779 A1   6/2013 Notohara

FOREIGN PATENT DOCUMENTS

WO    2010/143082    12/2010
WO    2015/061582     4/2015

* cited by examiner

COMPUTING AND DISPLAYING A SYNTHETIC MAMMOGRAM DURING SCANNING ACQUISITION

CROSS REFERENCE TO RELATED APPLICATIONS

This application is the U.S. National Phase application under 35 U.S.C. § 371 of International Application No. PCT/EP2016/081098, filed Dec. 15, 2016, published as WO 2017/108549 on Jun. 29, 2017, which claims the benefit of European Patent Application Number 15201478.3 filed Dec. 21, 2015. These applications are hereby incorporated by reference herein.

FIELD OF THE INVENTION

The invention relates to an image processing apparatus, to an image processing system, to an image processing method, to a computer program element and to a computer readable medium.

BACKGROUND OF THE INVENTION

Mammography imaging systems are one of the mainstays in fighting cancer. Accurate high quality imagery allows early detection of cancer in the breast and thus allows saving the lives of many women. Useful as these imaging systems are, they still use x-ray radiation which on its own poses dangers for health. It is therefore an important consideration in image based diagnostics that each dosage incurred should add value. For instance the imagery obtained by any x-ray exposure should be of the highest quality and relevance to the task at hand. It has been observed however that the problem of producing low quality imagery or irrelevant imagery for a certain task at hand is still prevalent among the medical community.

SUMMARY OF THE INVENTION

It is therefore proposed the system or method to at least facilitate production of high quality imagery and/or relevance of imagery so produced.

The object of the present invention is solved by the subject matter of the independent claims where further embodiments are incorporated in the dependent claims. It should be noted that the following described aspect of the invention equally applies to the image processing method, the image processing system, to the computer program element and to the computer readable medium.

According to a first aspect of the invention there is provided image processing apparatus, comprising:

an input port for receiving projection data through respective 3D locations in an imaging region, said projection data collected in a scan operation by an imaging apparatus;

an image segment generator configured to generate, based on said projection data, a first image segment for said 3D locations; and a visualizer (VIZ) configured to effect displaying said first image segment on a display device before or whilst projection data for a different 3D location in the imaging region is being received at the input port. In particular, the displaying of the first image segment is effected before or whilst the image apparatus collects projection data for a different 3D location. Said first image segment forms only a (spatially) partial image of a complete image.

In one embodiment, the image segment generator includes an image reconstructor and an image synthesizer. The reconstructor is configured to reconstruct, based on said projection data, respective first volume segments for said 3D locations. The synthesizer configured to compute the first image segment from said first volume segments. However this is one embodiment and a computation of the 2D image segment purely in projection domain is also envisaged.

In other words, in either embodiment, the proposed system allows for producing relevant imagery more efficiently. The proposed system allows providing visual feedback on the acquired scan data whilst the scan operation is still ongoing. The image segment is a true sub-set of the complete image (also referred to herein as the "verification image") that is being built up gradually (from subsequent image segments) already during the scan operation. The verification image is for the whole of the imaging region whilst the image segments cover only respective, different parts of the imaging region. The "growing" verification image allows a user (e.g., a radiologist) to verify at an early stage during the scan whether an acceptable image quality or relevance has or will be achieved. If not, the image acquisition does not have to run to the end and can be aborted earlier thus saving dosage otherwise wasted on irrelevant and low quality imagery. In short, in the proposed system, projection data acquisition and visualization thereof occur quasi-concurrently in quasi-real-time (relative to the projection data acquisition).

More specifically and according to one embodiment, the reconstructor operates to reconstruct for different 3D locations respective second image volumes, wherein the synthesizer operates to compute a second image segment, said second image segment forming another partial image of the complete image, and the visualizer operates to accumulatively display the second segment together with the already displayed first image segment. The two (or more) segments are (spatially) partial in the sense that they represent different 3D image locations. The 3D locations for the first segment are not represented in the second segment and the 3D location(s) for the second segment are not represented in the first segment, and so on for more image segments. The image segments are complementary. Only when the two (or generally more) image segments are eventually displayed together in accumulation does the complete image form. The image segments eventually together "tile" the complete image.

In this accumulative fashion a complete picture can be gradually build up and displayed to the user whilst the data collection operation unfolds. At least (spatially) partial image information as per the verification image can provided to the user as soon as this partial information is available in the scan.

According to one embodiment, the image segment is an image strip but representations in other shapes are also envisaged.

According to one embodiment, the image visualizer is configured to compute a display time (or time delay) for a current image segment. According to one embodiment, the display time is computed as a function of any of the following parameters: a speed of the scan operation of the imaging apparatus, the measured projection data, a time required to compute the image volume segments, the computed image volume segment, or the time required for the second image segment to be displayed. Each of these parameters can be thought to represent a tell-tale for image content complexity. Further methods for computing the image content complexity can be derived for example from a Shannon entropy measure, edge response filters, brightness (intensity) values, histogram measures, or CAD (Computer-aided Detection) features. The display time can thus be adapted to the expected complexity in the image segments. This allows the user to better judge whether it is worth waiting for a next image segment to be reconstructed and/or displayed.

According to one embodiment, the 3D location is defined in a coordinate system having geometry that corresponds to a geometry of a scan operation. In particular, if the scan operation is performed along a circular arc, a cylindrical coordinate system is used with origin in the focal spot of an X-ray source of the imaging apparatus. This allows saving CPU time. The system and method proposed herein is not limited to circular paths, as other curved (not necessarily circular) or linear paths (or a combination thereof) are also envisaged herein.

According to one embodiment, the imaging apparatus is a slit-scanning imaging apparatus, in particular, a mammography slit-scanning imaging apparatus.

According to a second aspect there is provided a system comprising an image processing apparatus of any of the previously mentioned embodiments, further comprising the imaging apparatus and/or the displaying device.

According to a third aspect, there is provided an image processing method comprising:

receiving projection data through respective 3D locations in an imaging region, said data collected in a scan operation by an imaging apparatus (IM), collecting;

based on said projection data, generating a first image segment for said 3D locations; and before collecting projection data for a different 3D location or whilst so collecting, displaying said first image segment on a display device.

According to one embodiment, the method further comprises the step of generating for different 3D locations, including said different 3D location, a second image segment and accumulatively displaying same with the displayed first image segment.

According to one embodiment, the generating step includes a tomosynthetic reconstruction.

BRIEF DESCRIPTION OF THE DRAWINGS

Exemplary embodiments of the invention will now be described with reference to the following drawings wherein.

DETAILED DESCRIPTION OF EMBODIMENTS

Figure 1:
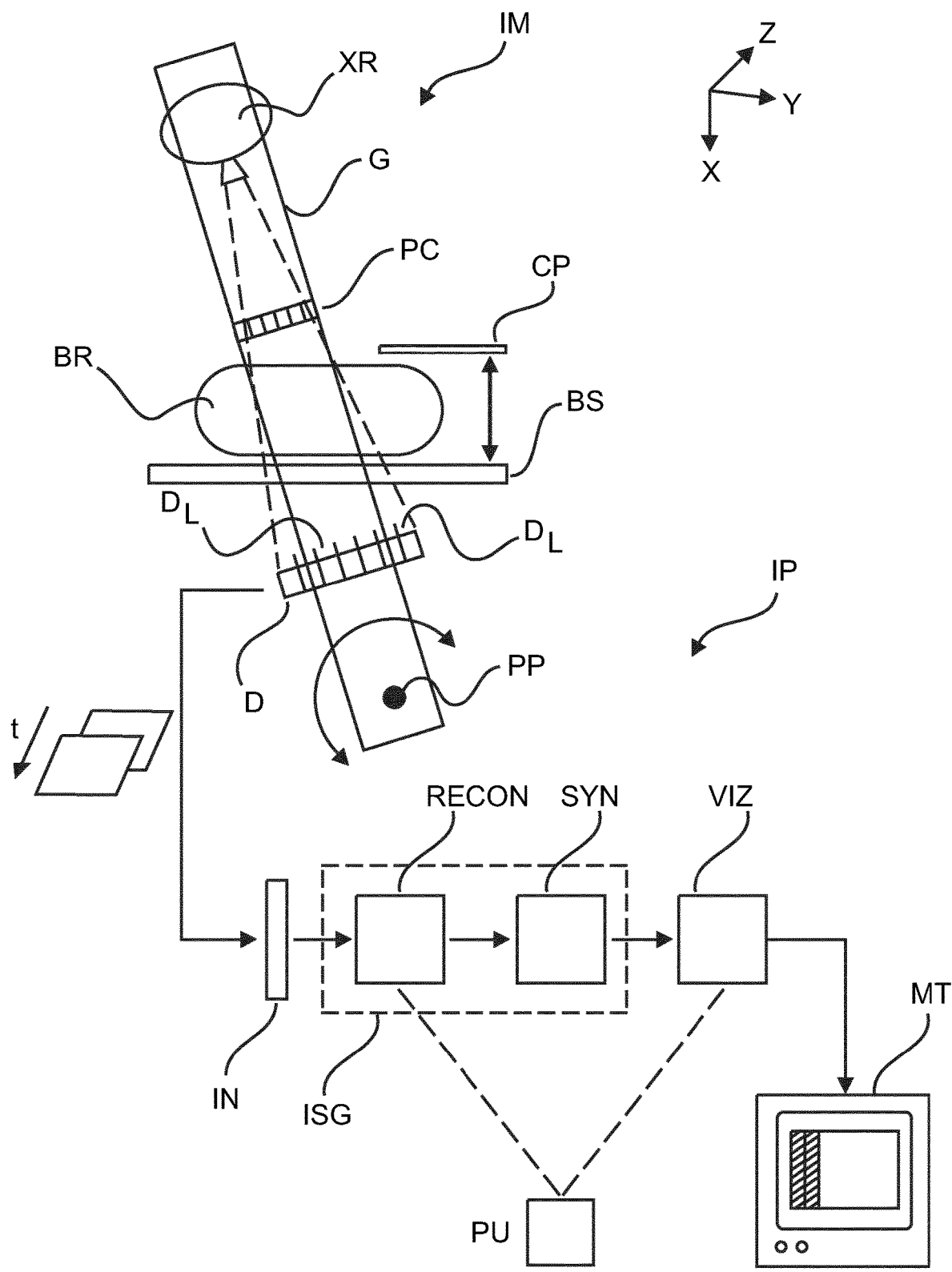
FIG. 1 shows an imaging arrangement.

With reference to FIG. 1 there is shown an imaging arrangement as envisaged herein. The imaging arrangement includes an x-ray imaging apparatus IM and an image processing apparatus IP for processing imagery supplied by the imaging apparatus IM. Preferably, the imagery is supplied direct and/or in real-time from the imaging apparatus IM. Even when the imagery is supplied in real-time from the imager IM via suitable interfaces, this does not exclude storage in a buffer memory and/or concurrent forwarding of copies of the received imagery to permanent storage such as image database, PACS or other memory.

The imaging apparatus IM is envisaged to be of the scanning type. More particularly and according to one embodiment the imaging apparatus IP is a mammography scanner of the slit scanning type but imagers for other than mammography applications are also envisaged. Furthermore, even when the imager IM is for mammography, it may not necessarily be of a slit-scanning system, as other imaging technologies are also envisaged herein.

As its basic components the scanner includes a movable gantry G which is rotatable around a pivot point PP. In another embodiment, the motion of the gantry G is realized by a guardrail and an actuator. The Furthermore, the pivot point is not necessarily fixed. In the gantry there is fixedly arranged an X-ray source XR and opposite therefrom, an X-ray detector D module. The detector D includes a plurality of discretely spaced apart detector lines DL, each comprising a plurality of imaging pixels that extend perpendicularly into the drawing plane as per the frontal side elevation view afforded by FIG. 1. In one embodiment, the detector module D includes about 20 detector lines (in one embodiment there are 21 detector lines) but this is exemplary as more than 20 detector lines or less than 20 detector lines are also envisaged.

Because of the scanning setup mainly envisaged herein, the movable gantry will be referred to herein as a "scan arm". The scan arm motion may also be realized as a combination of a translation and a rotation.

An imaging region is defined between the x-ray source XR and the detector D. The imaging region is suitably arranged to receive an object to be imaged. As used herein, said object may refer to an animate or inanimate object. An inanimate object may be examined in non-destructive material testing or during security scans at airports, etc. An animate "object" is a part or the whole of a human or animal patient. In particular, the object as mainly envisaged herein is a human breast and this is what will be referred to in the following merely for illustrative purposes, with the understanding that imaging applications in relation to inanimate objects or other parts of the human or animal anatomy are not excluded herein.

In mammography embodiments, there is a breast support BS for receiving and supporting a breast BR. A slideable compression plate CP exerts pressure on the breast during an imaging acquisition to improve image contrast. In non-mammography contexts, the examination region includes any type of suitable support for supporting the object to be imaged. For instance, a patient table may be arranged for the patient to lie on so that a desired region of interest (ROI) can be imaged. In other embodiments, the imaging region is merely a portion of space in a room where the object or patient resides during the imaging, in particular the patient may stand upright during the imaging, such as in chest scans.

In one embodiment, there is also a pre-collimator arrangement PC that collimates radiation passing there-through so as to divide a radiation beam emitted by the source XR into a plurality of partial beams each aligned with a corresponding one of the detector lines DL.

During an imaging acquisition, the scan arm G, together with the detector D and/or the x-ray source XR, trace out a scan path in a scanning motion. The scan path may be traced out in a complete or preferably partial rotation around the breast BR. Indeed, in tomosynthetic imaging mainly envisaged herein only an arc is traced in an exemplary angular interval of up to 100°-200°. This is however not limiting as the scan path or scan trajectory may not necessarily be curved. For instance, a scan path along a straight line is also contemplated in some embodiments. The scan speed is usually uniform but embodiments are envisaged herein where the scan speed is non-uniform, for example when using an automatic exposure mode. More particularly, in one embodiment the scan speed along the path varies with a density of the tissue irradiated. The density can quickly be computed based on the projection data currently detected at a given position of the scan path.

Specifically and in the tomosynthetic embodiment mainly envisaged herein, the detector proceeds on the scan trajectory in an arc during the scanning motion and is scanned past the breast from underneath whilst the detector receives radiation from the x-ray source after passage through the collimator and through the breast tissue. Again, it will be understood that a tomosynthesis imaging system shown in FIG. 1 is merely exemplary. In other systems the pivot point is located not under the breast but above it. Furthermore, in other systems the motion of the scan arm is realized without any pivot point but by using guiderails and actuators.

Whilst scanning along the scan path, a set of projection data π is acquired from a plurality of different locations along the path. The plurality of projection data collected from different positions encodes depth information. This depth information is processed by a suitable tomosynthesis algorithm into 3D image data.

In more detail and with continued reference to FIG. 1, the projection data is forwarded to an input port IN of the image processing apparatus IP.

The projection data from the different positions along the path is then reconstructed into different volume segments which correspond to different 3D locations in the imaging region where the breast resides. An image segment generator ISG generates from the projection data a plurality of image segments. Each segment affords only a respective partial view of the breast whereas the image segments together affords a complete picture of the breast. The partial view of a given segment corresponds to the information in the projection data collected at certain angular positions on the scan path. Some or all of the image segments can be displayed by operation of a visualizer VIZ on a display device such as computer monitor MT.

In yet more detail, image segment generator ISG includes in one embodiment a 3D reconstructor and an image synthesizer SYN. Conceptually, the imaging region is made of 3D locations (voxel) organized in a suitable imaging region coordinate system. The reconstructor uses a reconstruction algorithm, which computes a respective image volume segment made up of voxels. The 3D image volume segment so computed by reconstructor RECON is, as such, difficult to represent on the 2D image plane of the monitor MT. It is therefore the task of the synthesizer SYN to compute a suitable 2D representation or rendering for the voxel data. Generally, the synthesizer SYN computes a forward projection through the voxels and onto the 2D image plane to produce the plurality of image segments. Each image segment forms a part of a synthetic mammogram which can be compiled from the image segments. The visualizer VIZ is used to map individual image points in the segments to respective color or grey values. The visualizer VIZ further operates to compile the image segments in a manner described in more detail further below and interfaces with video driver circuitry to effect displaying of the image segments on the monitor MT. The functionalities of the reconstructor RECON and of the synthesizer SYN can be merged into one functional unit. In this case, the 2D rendering of the image segment is produced direct from the projection data without computing first the 3D volume segment for the voxels. This can be achieved by avoiding non-linear operations in the 2D image segment generation.

However, very much unlike previous approaches in tomosynthesis imaging, it is proposed herein to compute and display the synthetic mammogram (substantially immediately) during data acquisition in the scanning operation and to update the currently displayed imagery on monitor MT at certain time intervals during the progression of the scan projection data acquisition. In this manner visual feedback on the scanning procedure is provided by way of a "verification image" which is gradually built up from the computed image segments as scanning motion by the scan arm is ongoing. The user quasi-immediately (with a certain delay which will be explained in more detail below)—provided with a visual clue on how a respective part of the tomosynthesis image is going to look like. Specifically, the image segment generator operates together with the visualizer VIZ to gradually build up the complete verification image from the image segments one by one in accumulation until the projection data collection concludes and the complete synthetic mammogram is displayed. The user can then thus see earlier whether the tomosynthesis image is going to have clinical value for the task at hand and if this is not the case, can abort the data acquisition thus saving patient dosage. Dosage wasted on potentially useless imagery can thus be avoided or minimized. In the proposed system we make use of the fact that in certain tomosynthesis systems such as the slit scanning acquisition shown in FIG. 1, an essentially simultaneous measurement of fan beam projections by the plurality of line detectors is performed from different angulations for any given position of the scan arm and hence the detector lines.

Figure 2:
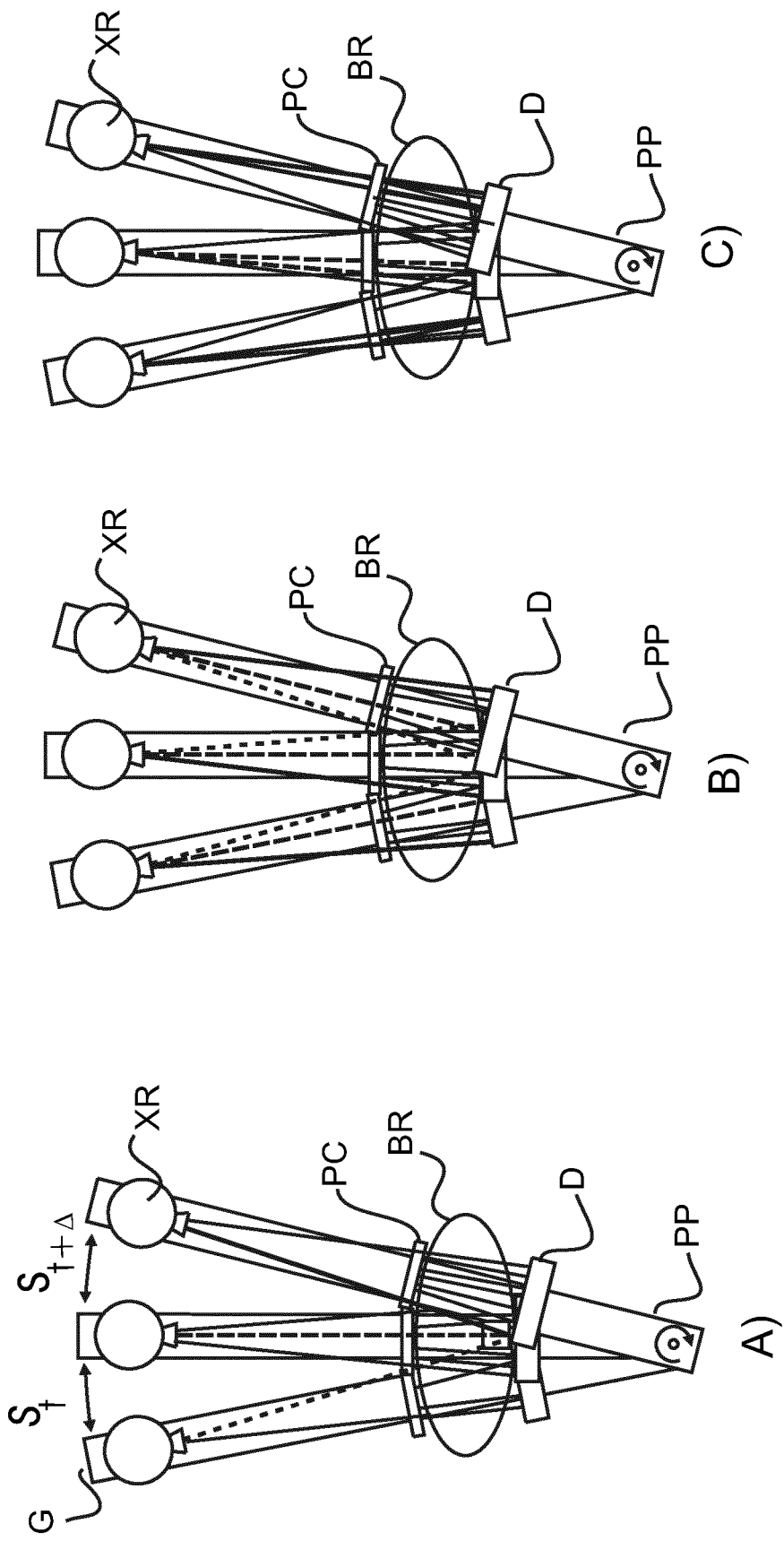
FIG. 2 shows an imaging geometry for a scanning operation.

The extraction of 3D or depth information from the collected projection data is richer the more detector lines have seen a given 3D location from different positions on the scan path. The phrase that a given 3D location/voxel is "seen" by a detector line is used herein as a convenient and suggestive shorthand for the geometrical situation where, for a given detector line at a given position on the scan path, one can draw an imaginary line ("ray") from said detector line to the focal spot of the X-ray source XR, and this line passes through said 3D location. This is illustrated for instance in FIG. 2A, showing more detail of the scanning geometry. The small square in the breast region shows a certain voxel. It can be seen that after the scan arm has covered a path length $s_t$ along the scan path, we already have sufficient information to extract depth information for this voxel because said voxel has been seen in at least two (in fact three) views by at least two (three) detector lines along corresponding rays shown as dotted and dashed lines. In other words, the reconstruction of the volume segment by reconstructor RECON for this location and the synthesizing by synthesizer SYN of the 2D image segment from the volume segment can commence already at the time instant when the scan arm assumes the position $s_t$ along the scan path at time t. In the simple case of a circular trajectory (as exemplary shown in FIG. 2), the path length can be parameterized by an angle.

Figure 3:
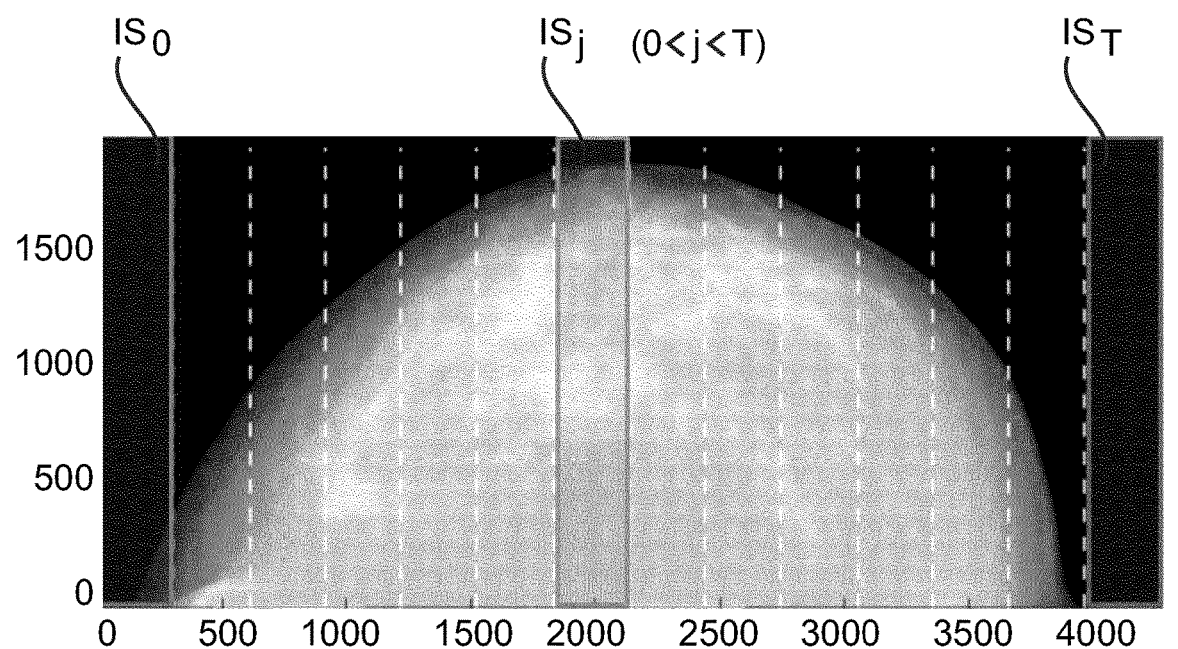
FIG. 3 shows an illustration of an accumulative displaying of image strips.
Figure 3:
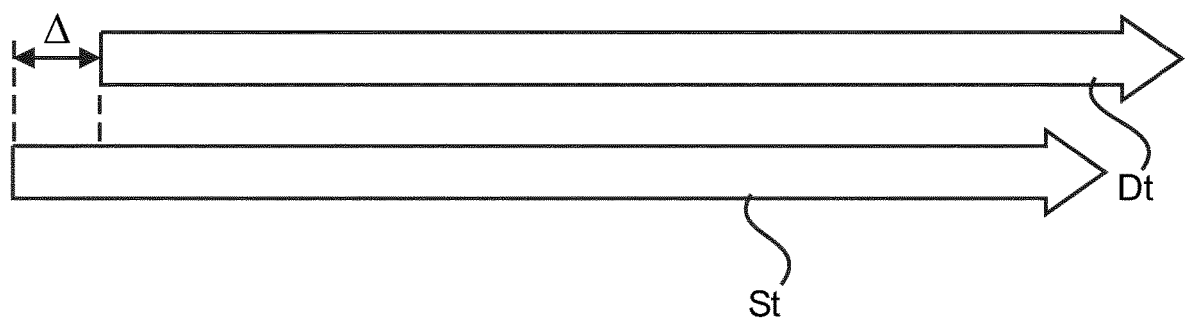

The image segment generator performs its operation preferably simultaneously for other voxel positions which have been seen by at least two different detector lines. The collection of 2D image points so generated can then be consolidated into an image strip forming one image segment of the verification image. The verification image can then be built-up one by one in an accumulative fashion as the scanning is performed. That is the strips IS are displayed in sequence in which they are being computed alongside each other by operation of the visualizer VIZ as shown in FIG. 3.

The richness of the 3D or depth information extractable from the projection data per voxel can be enhanced of course by waiting for the instant when said voxel has been seen by more than two detector lines, such as three (or more) as shown in FIG. 2A. For instance, if one waits for the detector to trace out a path-length $s_{t+\Delta}$ along the scan path at a later time $_t+\Delta$, the voxel has then been seen by even three detector lines. In one extreme embodiment, the generation of the image strips is delayed until the relevant voxels have been seen by all detector lines to generate a high-quality verification image. The proposed system may therefore provide suitable user input functionalities with which the user can set the minimum number of detector lines from which a voxel has to be seen for the reconstruction and synthesizing to commence. The higher this number is set, the longer the delay will be for the respective image strips to be visualized, but the better the 3D information extraction. However, if promptness of visualization is a premium, one may simply wait until the voxel has been seen by a single detector line in which case the visualization in the image segments merely amounts to a visualization of the projection data itself. In this very simple embodiment, the image segment generator ISG simply reproduces the projection data during the collection, and this is then visualized. To co-ordinate the operation of when the generation of the respective image segment is to commence, the system further includes a geometrical tracking component (not shown) that tracks for each voxel position and throughout the scan operation the number of detector lines that have seen the respective 3D location from at least N positions (N≥1, but preferably N≥2). Once the respective 3D location has been seen by at least N detector lines, a flag is set for that respective 3D location. A signal is then issued forth to the re-constructer to reconstruct, from the respective part of the projection data, the 3D volume segment. The synthesizer then operates to synthesize a corresponding 2D image point for the image strip to be displayed. This 2D image point computation is done for each image 3D location which has been seen by the required number of detector lines and the collection of the so synthesized image points is then displayed by operation of the visualizer on the monitor as an image segment, e.g. a strip or other shape. The same is done for other 3D locations to obtain other image segments, and these are then displayed one-by-one, in accumulative fashion on the monitor MT.

The reconstruction implemented by reconstructor RECON may be as simple as an unfiltered back-projection (also referred to and shift-and-add operation) but a more involved filtered-back-projection scheme or an iterative reconstruction algorithm may also be used instead if required. Also, to improve the computation time, the imaging region co-ordinate system is preferably adapted to the geometry of the scan motion. For instance, if the scan motion proceeds along an arc, a cylindrical co-ordinate system is advantageous. The synthesizing algorithm used by the synthesizer SYN may include, for instance, maximum intensity projection schemes, linear or non-linear summing of voxels along rays, or more complex CAD (computer-aided-detection) based techniques as described in tomosynthesis literature.

As a refinement of the above, the reconstruction and the synthesizing operations for earlier image strips may be revisited during the remainder of the scan operation as the respective locations are seen by more detector lines. In this way the 3D content of the earlier displayed image strips can be improved during the scanning.

FIG. 3 is a time-resolved illustration of how the verification image is built up from the image strips during the scanning. The numbering indicates pixel position in vertical and horizontal directions. The two arrowed timelines show the scan time St and the display time Dt. As can be seen, there is a time delay $\Delta$ of display time which corresponds to the time needed to ensure that a respective 3D location has been seen by the required number of detector lines (for instance two or more). The build-up of the verification image commences with the first strip to the very left $IS_0$, then proceeds through intermediate image strips $IS_j$ and concludes with the last image strip $IS_T$. Of course, verification image may be built up from right to left or vertically from top to bottom (or vice versa) if required. The computed image segments points may not necessarily be organized in image strips. Other geometrical shapes are also possible. In fact, the verification image may be built up as an "image point cloud" gradually growing from one side of the 2D image plane of the monitor MT to the other. As can be seen, in either embodiment, the verification image is gradually completed as the individual image segments ISj (e.g., strips) are displayed one after, and in addition to the other. Portions of the image plane remain blank until filled with the respective image segments once enough projection data from the required number of different detector lines (or from the same detector line from different positions) on the scan path have been collected. In other words, the image segments IS are displayed in quasi-real-time (save for the delay $\Delta$) during the scan operation.

As mentioned, although it may be sufficient for a certain 3D location to be seen from merely two detector lines in different positions, the being seen from more than two detector lines may be required in other embodiments and in fact in one embodiment the computing of the image strip commences only once the respective 3D locations have been seen by all detector lines. This last embodiment however will entail that delay $\Delta$ in FIG. 3 is maximal. In either embodiment, the maximum delay to be expected will be in the range of about 20% of the total scan time for slit-scanning system of the type shown in FIGS. 1, 2. If one generates the image segments merely from two detector lines, one can even reduce the display delay $\Delta$ to only about 1% of the total scan time.

Figure 5:
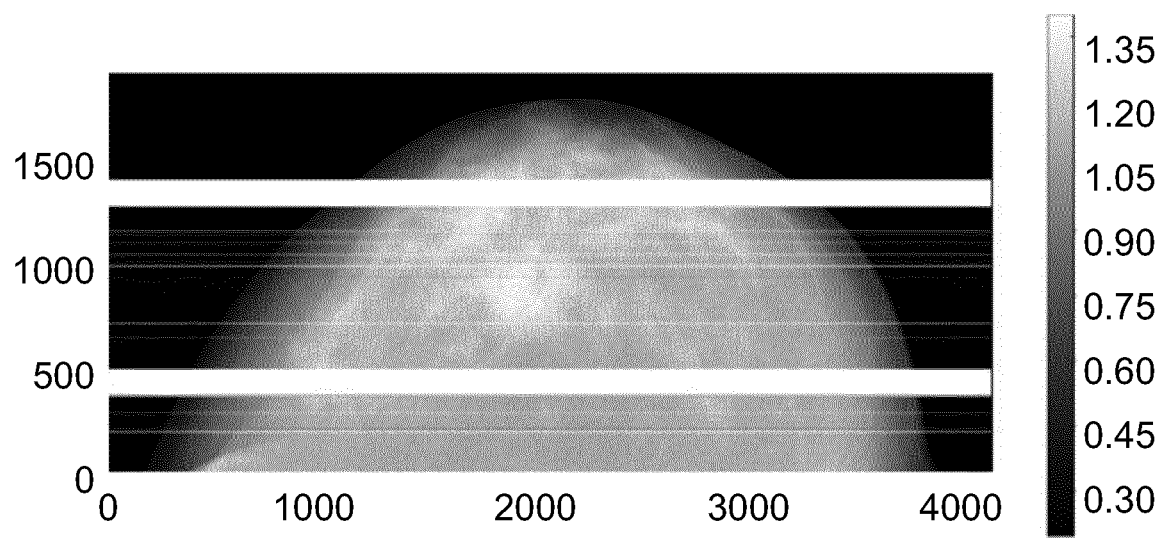
FIG. 5 shows an illustration of imagery reconstructed from incomplete projection data and an image suitably interpolated to substitute missing image information.
Figure 5:
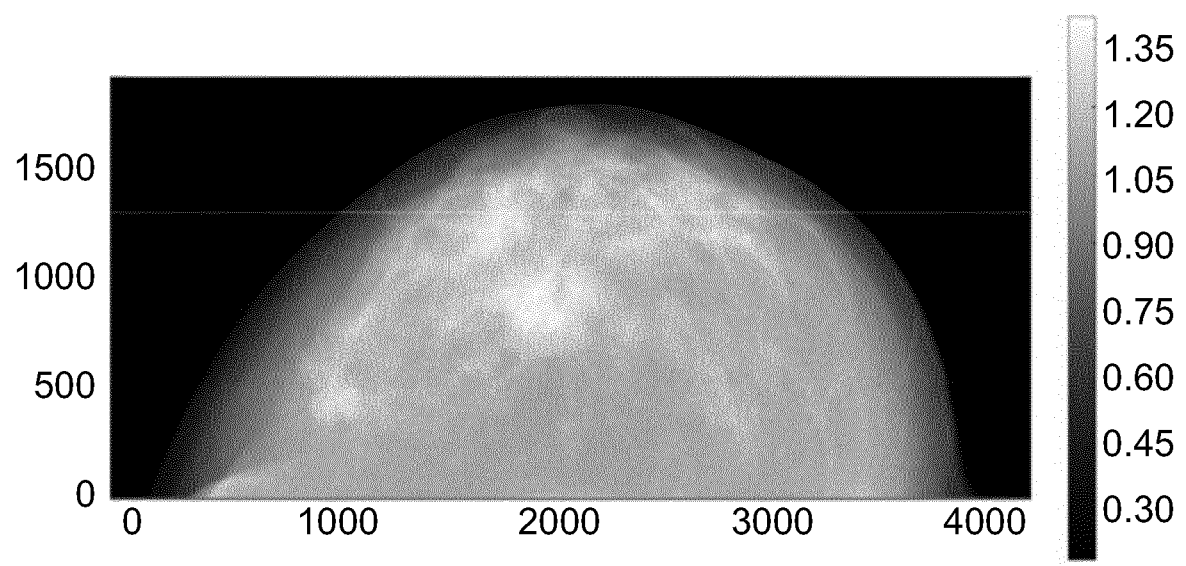

In one embodiment, the proposed system IP is configured to deal with a complication which occasionally arises in relation to the manufacturing requirements of the detector lines. Namely, in some embodiments, the respective pixels of a detector line are not arranged quasi-continuous but include gaps in between groups of detector pixels. If the previously described method were to be applied to projection data collected by gapped detector lines, one would obtain a situation as shown in FIG. 5A where the back projected data inherits the gaps in the projection data due to gaps in the detector lines. To arrive at "smoothed" verification imagery as shown in FIG. 5B, the proposed system includes an interpolation scheme in which the respective image segments are generated based on projection data combined from two (or more) neighboring detector lines.

More particularly, a synthetic 2D projection image segment is generated by combining data from neighboring pairs of line detectors (immediately) during data acquisition as follows. For each scan-arm position, the data from two neighboring line-detectors are back-projected onto, preferably, but not necessarily in all embodiments, a cylindrical grid. Back-projection may be done by shift-and-add reconstruction although more involved filtered back-projection or other reconstruction techniques such as iterative reconstruction algorithms may be used. By combining projection data from neighboring lines and by reconstructing the so combined projection data in this way, the missing data gaps (FIG. 5a) can be eliminated (as in FIG. 5b). Afterwards, the data is forward-projected onto the desired image plane to commonly synthesize the image segment information. The image plane can be defined via averaged geometry coordinates of both line detectors. Since the angular difference between the neighboring line detectors is very small, only few radial layers have to be reconstructed. Furthermore and due to the rotational symmetry of the imaging geometry as illustrated in FIG. 2B, a simple shift-and-add back and forward-projection can be used for a computationally efficient implementation when using a cylindrical imaging geometry.

An additional improvement of computational performance can be achieved by using the data from the second line detector only to fill the gaps of the first detector. This can be done because the gaps are usually staggered, so the lack of projection information as collected by one detector line, can be filled by interpolation using projection information collected from a neighboring detector line where there is no gap. In other words, in this embodiment not all of the projection data from one detector lines are combined with projection data from the other, neighboring one. Only the respectively missing data chunks are combined into the neighboring detector lines.

More specifically, at scan start, the two outmost line detectors on the left side of the detector unit (see the solid lines in FIG. 2C) are combined into a 2D strip image (shown as the left Image strip $IS_0$ in FIG. 3) until data from the next (i.e. from the 3rd) line detector is available. Then, the data from the 3rd line detector is used instead of the first line detector data and so on. At the end of the scan, the data of the two outmost line detectors on the right side of the detector unit (shown as dotted lines in FIG. 2C) are used to combine the final strip (strip $IS_T$ in FIG. 3) of the 2D verification image. In this way, the synthetic projection image of the complete field-of-view can be generated without any data gaps.

The combining of projection data from the two neighboring lines can be refined by using interpolation techniques instead of a sharp transition when switching from one line detector to another. Although using two detector lines that are immediate neighbors as shown in FIGS. 2B, C is the preferred embodiment, one may also combine instead detector lines that are further apart.

As is the case for embodiment where the detector lines are gap-free, the generation of the image segment may be computed directly in the projection domain rather than, as described above, back-ward and forward-projecting between image and projection domain.

In one embodiment, the visualizer is configured to compute an individual display time for the currently generated image segment. This display time is the (additional) time delay at which the next segment $IS_{j+1}$ will be displayed on the monitor MT. This delay is counted from the instant the earlier segment ISj is being displayed. In other words, if $T_j$ is the instant when segment $IS_j$ is displayed and if $T_{j+1}$ is the (later) instant when $IS_{j+1}$ is displayed, then the "display time" for the later segment $IS_{j+1}$ is $\Delta_{DT}=T_{j+1}-T_j$. The display time can be computed in dependence on different parameters. For instance, if the scan speed is dependent on the density of the tissue currently scanned, then the display time can be computed proportional to the actual scan speed with which the projection data for the respective image segment has been collected. See for instance M. Åslund et al in "AEC for scanning digital mammography based on variation of scan speed", Medical Physics, 32(11), 3005, pp. 3367-74. In addition or instead, the parameter may include any one or a combination of the following: i) the measured projection data, ii) the computed image volume segment, or iii) information content in the image segment to be displayed. Information content can thus be gathered in projection domain, image domain or in the synthesized image. In each case, information content can be assessed based on entropy or on other information theoretic concepts using edge response filters, brightness (intensity) values, histogram measures, CAD (Computer-aided Detection) features and the like. In another embodiment, the display time is computed to be a function of the estimated average breast thickness at the current volume segment. The local breast thickness estimates can either be measured from spectral mammographic data or estimated by fitting a breast shape model to the measured projection data.

An effect of using a display time in this manner is that segments IS with more complex information content are being displayed longer before the next segment is displayed. This allows focusing the user's attention to potentially more relevant or interesting image features: image strip that mainly encode background are likely to be of lesser relevance than those that encode more actual tissue information.

The components of the image processing system IPS may be implemented as software modules or routines in a single software suite and run on a general purpose computing unit PU such as a workstation associated with the imager IM or a server computer associated with a group of imagers. Alternatively the components of the image processing system IPS may be arranged in a distributed architecture and connected in a suitable communication network.

Alternatively some or all components may be arranged in hardware such as a suitably programmed FPGA (field-programmable-gate-array) or as hardwired IC chip.

Figure 4:
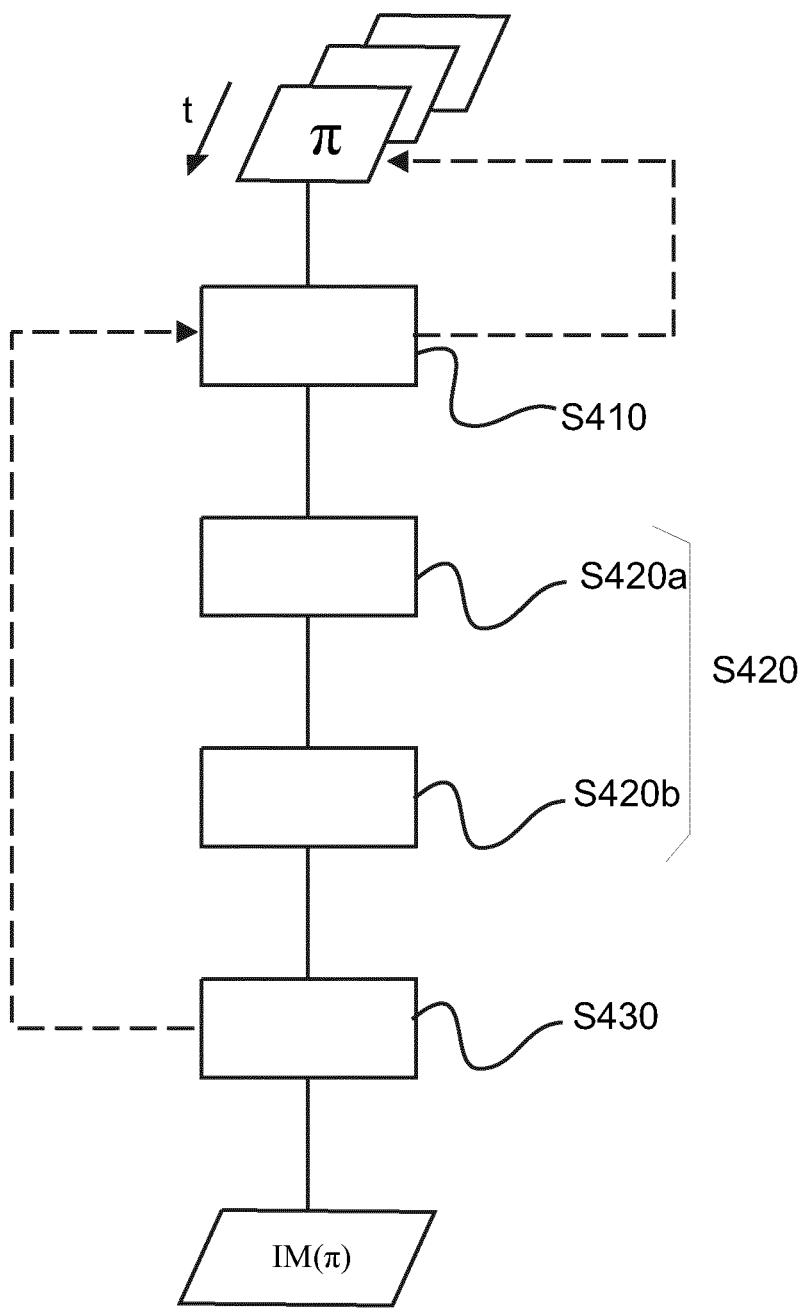
FIG. 4 shows a flow chart of an image processing method.

Reference is now made to the flow chart of FIG. 4 where an image processing method underlying operation of the image processing apparatus in FIG. 1 is described. However, those skilled in the art will understand that the following method steps are not necessarily tied to the architecture shown in FIG. 1. In other words, the following description in relation to flow chart in FIG. 4 constitutes a teaching in its own right.

At step S410, projection data π is received. The projection data π is measured by projection of X-ray radiation through respective 3D locations in an object to be imaged, said object residing in an imaging region. The projection data is collected in a scan operation by an imaging apparatus such as a slit-scan mammography apparatus or other. In one embodiment, the imaging apparatus includes a detector with a plurality of detector lines and this detector is scanned past the object so as to measure projection data through the respective 3D locations from different positions along a scan path.

At step S420, a 2D image segment is generated in a 2D image plane. According to one embodiment (but not all embodiments) this operation includes backward S420a and forward-projections S420b.

Specifically, at step S420a, a respective first volume segment is reconstructed in image domain for the respective said 3D locations, based on at least a part of the projection data collected in step S410. In particular this step includes collecting projection data from at least two different positions on the path. In one embodiment, the projection data is collected from more than two (eg, three) or from all possible, different positions along the scan path to maximize 3D content extraction.

The reconstruction may be implemented as a simple unfiltered (shift-and-add) back-projection and/or the imaging region coordinate system may be adapted to symmetries, if any, of the scan path. Both afford fast computation.

At step S420b, a first image segment is synthesized from the said volume segments. This step can be based for instance on maximum intensity protection schemes or linear or non-linear weighted summing of volumes or more complex CAD techniques. Essentially the synthesizing operation corresponds to a forward projection through the reconstructed 3D volume segments onto the 2D image plane that corresponds to the image plane in which the segment is to be displayed on a 2D display device, such as a computer monitor. In other words, the task of the synthesizing step is to translate the 3D or depth information embodied in the reconstructed 3D volume segments into a representation on in the 2D image plane.

The image segments (eg, individual strips) so generated form visual sub-components of a verification image in that plane. The location in space of that the 2D plane is user adjustable in one embodiment.

In one embodiment, image segment generation step S420 is done entirely in the projection domain without sojourning via back-projection into the (3D) image domain. Instead, the effect of the back- and forward-projection operation is directly computed in the projection domain by deriving a set of equivalent 2D filters on the projection data using the linearity of the back- and forward projection operators.

In a very simple embodiment, the image segment generation step S420 is based on reproducing the projection data itself for the respective voxels during the projection data collection. The visualization responsiveness is thus maximal but the 3D information is then not available as each voxel has been merely seen by a single detector line positon along the scan path. Preferably, the image generation S420 is based on projection data seen from at least two detector-lines or more (eg, three), or even more preferable, by all detector lines to maximize 3D information content encoded by the generated segments.

In combination with any of the above embodiment, the method includes a scheme to compensate for imperfections in the detector, in particular for pixel gaps on certain or all detector lines. Interpolation is used in one embodiment, where the image segment generation (in particular the reconstruction) is based on pairs of neighboring detector lines.

At step S430 the generated image segment is then displayed on a screen.

More particularly the generated segment is a true sub-set of the complete verification image which is to be built up by the proposed method. More particularly, it is only this sub-set (together with earlier display image segments, if any) that is displayed once the current image segment has been generated. In particular, and to update the verification image as quickly as possible, the current image segment is already displayed before or whilst the scan operation proceeds to collects projection data for different 3D locations.

More particularly, the previous steps S420 (in particular sub-steps S420a,b if applicable) are repeated for a different, second image location so as to display in an accumulative fashion the newly generated second image segment together with the first image segment. These steps are repeated throughout the remainder of the scan operation until the last image strip is displayed thus finally providing to the user the complete verification image at the conclusion of the scan operation.

In one embodiment the imaging apparatus varies its scan speed automatically, in dependence on the density of the imaged tissue. This additional information can be used by correspondingly varying a display time of the respective strips. The display time is computed to be proportional to the actual scan time for the respective image segment $IS_j$. More particularly the display time is computed as a function of any of the following parameters: speed of the scan operation, the measured projection data, the computed image volume segment data, the time required to computed the image volume segments (if any), or the time required to compute image segment to be displayed. Either of these parameters can be used as a basis to adapt the display time to the expected complexity of the image content encoded in the respective image segment. In other words, the more complex the image information in the respective image strip, the longer the delay is until the next subsequent image strip is being phased in for display alongside (in accumulation) with the currently displayed image segment/strip.

The individual widths of the image segments are in one embodiment user adjustable. Furthermore, the widths may not necessarily remain constant during the accumulative displaying although image segments with constant widths are preferred.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium (in particular, but not necessarily, a non-transitory medium), such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An image processing apparatus, comprising:
   an input port for receiving projection data through respective 3D locations in an imaging region, the projection data being collected in a scan operation by an imaging apparatus;
   an image segment generator configured to generate, based on the projection data, a first image segment for the 3D locations; and
   a visualizer configured to effect displaying the first image segment on a display device before or while projection data for a different 3D location in the imaging region is being received at the input port, the first image segment forming only a partial image of a complete image.

2. The image processing apparatus of claim 1, wherein the image segment generator operates to generate for different 3D locations a second image segment, said second image segment forming another partial image of the complete image, and the visualizer operates to accumulatively display the second image segment together with the already displayed first image segment.

3. The image processing apparatus of claim 1, wherein the image segment is an image strip.

4. The image processing apparatus of claim 1, wherein the image visualizer is configured to compute a display time for a current image segment, said display time being the time delay at which a next segment will be displayed on the monitor.

5. The image processing apparatus of claim 4, wherein the display time is computed as a function of any of the following: a speed of the scan operation of the imaging apparatus, the measured projection data, the computed image volume segment, a time required to compute the image volume segments.

6. The image processing apparatus of claim 1, wherein the 3D location is specified in a coordinate system whose symmetry corresponds to a symmetry of a geometry of the scan operation.

7. The image processing apparatus of claim 1, wherein the imaging apparatus is a slit-scanning imaging apparatus, in particular, a mammography slit-scanning imaging apparatus.

8. A system comprising an image processing apparatus of claim 1, further comprising the imaging apparatus and/or the displaying device.

9. An image processing method, comprising:
   receiving projection data through respective 3D locations in an imaging region, the projection data being collected in a scan operation by an imaging apparatus;
   based on the projection data, generating a first image segment for the 3D locations, the first image segment forming only a partial image of a complete image; and
   before or while receiving projection data for a different 3D location in the imaging region, displaying the first image segment on a display device.

10. The image processing method of claim 9, further comprising:
    generating for different 3D locations, a second image segment and accumulatively displaying same with the displayed first image segment.

11. The image processing method of claim 9, wherein the image segment is an image strip.

12. The image processing method of claim 9, wherein the 3D location is defined in a coordinate system having geometry that corresponds to a geometry of a scan operation.

13. The image processing method of claim 9, wherein the generating step includes a tomosynthetic reconstruction.

14. A non-transitory computer-readable medium having executable instructions stored thereon which, when executed by at least one processor, cause the at least one processor to perform an image processing method, comprising:
    receiving projection data through respective 3D locations in an imaging region, the projection data being collected in a scan operation by an imaging apparatus;
    based on the projection data, generating a first image segment for the 3D locations, the first image segment forming only a partial image of a complete image; and
    before or while receiving projection data for a different 3D location in the imaging region, displaying the first image segment on a display device.

* * * * *